United States Patent
Singer et al.

(10) Patent No.: US 11,426,431 B2
(45) Date of Patent: Aug. 30, 2022

(54) USING AUTOLOGOUS MESENCHYMAL STEM CELLS TO TREAT MULTIPLE SYSTEM ATROPHY

(71) Applicant: Mayo Foundation for Medical Education and Research, Rochester, MN (US)

(72) Inventors: Wolfgang Singer, Rochester, MN (US); Phillip Low, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/736,644

(22) PCT Filed: Jun. 15, 2016

(86) PCT No.: PCT/US2016/037632
§ 371 (c)(1),
(2) Date: Dec. 14, 2017

(87) PCT Pub. No.: WO2016/205371
PCT Pub. Date: Dec. 22, 2016

(65) Prior Publication Data
US 2018/0161374 A1    Jun. 14, 2018

Related U.S. Application Data

(60) Provisional application No. 62/175,628, filed on Jun. 15, 2015.

(51) Int. Cl.
*A61K 35/28* (2015.01)
*A61P 25/28* (2006.01)
*A61K 9/00* (2006.01)
*A61K 35/12* (2015.01)

(52) U.S. Cl.
CPC ............ *A61K 35/28* (2013.01); *A61K 9/0085* (2013.01); *A61P 25/28* (2018.01); *A61K 2035/124* (2013.01)

(58) Field of Classification Search
CPC .................. A61K 35/28; A61K 9/0085; A61K 2035/124; A61P 25/28
USPC ...................................................... 424/93.7
See application file for complete search history.

(56) References Cited

U.S. PATENT DOCUMENTS

| 2009/0214484 A1 | 8/2009 | Mironov |
| 2010/0129319 A1 | 5/2010 | Lindquist et al. |
| 2010/0166712 A1* | 7/2010 | Sadiq ................ C12N 5/0663 424/93.7 |
| 2010/0239540 A1 | 9/2010 | Brinchmann et al. |
| 2015/0023930 A1 | 1/2015 | Rawat et al. |

FOREIGN PATENT DOCUMENTS

| KR | 20150059671 | 6/2015 |
| WO | WO 2013/124815 | 8/2013 |
| WO | WO 2014/141219 | 9/2014 |

OTHER PUBLICATIONS

Oh et al., Phase I Trial of Repeated Intrathecal Autologous Bone Marrow-Derived Mesenchymal Stromal Cells in Amyotrophic Lateral Sclerosis, Stem Cells Translational Medicine, May 1, 2015, 4: p. 590-597.*
Kishk et al., Case Control Series of Intrathecal Autologous Bone Marrow Mesenchymal Stem Cell Therapy for Chronic Spinal Cord Injury, Neurorehabilitation and Neural Repair, (2010), 24(8): p. 702-708.*
Wenning et al., Development and Validation of the Unified Multiple System Atrophy Rating Scale (UMSARS), Movement Disorders, vol. 19, No. 12, (2004), pp. 1391-1402.*
Chen et al., "A safety study on intrathecal delivery of autologous mesenchymal stromal cells in rabbits directly supporting Phase I human trials," Transfusion, 55(5):1013-20, May 2015.
Lee et al., "Autologous mesenchymal stem cell therapy delays the progression of neurological deficits in patients with multiple system atrophy," Clin Pharmacol Ther., 83(5):723-30, May 2008.
Sotiropoulou et al., "Characterization of the optimal culture conditions for clinical scale production of human mesenchymal stem cells," Stem Cells, 24:462-471, Feb. 2006,.
Xi et al., "Preliminary report of multiple cell therapy for patients with multiple system atrophy," 22 Suppl 1:S93-9, Aug. 2013.
Zuk et al., "Multilineage cells from human adipose tissue: implications for cell-based therapies," Tissue Engineering, 7(2):211-228, Apr. 2001.
Extended European Search Report in European Application No. 16812338.8 dated Feb. 28, 2019, 281 pages.
Finke et al., "Multiple system atrophy masking multiple sclerosis," Clinical Neurology and Neurosurgery, 112:59-61, 2010.
Flabeau et al., "Multiple system atrophy: current and future approaches to management," Ther Adv Neurol Disord., 3(4):249-263, 2010.
Kuzdas-Wood et al., "Towards translational therapies for multiple system atrophy," Progress in neurobiology, 118:19-35, Jul. 2014.
Lee et al., "A randomized trial of mesenchymal stem cells in multiple system atrophy," Annals of neurology, 72(1):32-40, Jul. 2012.
Lee et al., "Bone Marrow-Derived Mesenchymal Stem Cell Therapy as a Candidate Disease-Modifying Strategy in Parkinson's Disease and Multiple System Atrophy," J. Clin. Neurol., 5:1-10, 2009.

(Continued)

*Primary Examiner* — Jennifer M. H. Tichy
(74) *Attorney, Agent, or Firm* — Fish & Richardson P.C.

(57) ABSTRACT

This document provides methods and materials for treating multiple system atrophy in a mammal. Specifically, the methods comprises intrathecally administering to the mammal a composition comprising autologous mesenchymal stem cells (e.g. adipose deprived mesenchymal stem cells) to treat multiple system atrophy. Further disclosed is the composition comprising from about 5×10(6) to about 5×10(8) autologous mesenchymal stem cells.

4 Claims, 6 Drawing Sheets

(56) References Cited

OTHER PUBLICATIONS

Li-ke et al., "Umbilical cord blood mesenchymal stem cell transplantation in 20 patients with multiple system atrophy," Chinese Journal of Tissue Engineering Research, 13(45):8975-8, Jan. 2009, English abstract.

Low and Gilman, "Are Trials of Intravascular Infusions of Autologous Mesenchymal Stem Cells in Patients with Multiple System Atrophy Currently Justified, and Are They Effective?," American Neurological Association, Jul. 4-5, 2012.

Low, "Mesenchymal Stem Cell Therapy in Multiple System Atrophy," clinicaltrials.gov, Dec. 11, 2014, retrived from [https://clinicaltrials.gov/ct2/show/NCT02315027], retrived on Apr. 3, 2019, 6 pages.

Palma and Kaufmann, "Novel therapeutic approaches in multiple system atrophy," Clin. Auton. Res., 25(1):37-45, Feb. 2015.

Singer and Low, "Mesenchymal Stem Cell Treatment in MSA—Rationale, Approach, and Early Experience," Abstracts / Autonomic Neuroscience: Basic and Clinical, 192:33-34, 2015.

Wang et al., "Clinical analysis of umbilical cord blood mesenchymal stem cells transplantation for treating multiple system atrophy in one case," Journal of Clinical Rehabilitative Tissue Engineering Research, 13(40):7955-7958, Oct. 2009, Abstract.

Singer, "Stem cell treatment in MSA: scientific basis, recent trials, and novel perspectives," 24th International Symposium on The Autonomic Nervous System., Clin. Auton. Res., 23:225-288, Oct. 2013.

Hurst et al., "Inflammatory hypertrophic cauda equina following intrathecal neural stem cell injection." Muscle Nerve, Nov. 2013, 48(5):831-835.

Low et al., "Are trials of intravascular infusions of autologous mesenchymal stem cells in patients with multiple system atrophy currently justified, and are they effective?," Ann. Neurology, Jul. 2012, 72(1):4-5.

* cited by examiner

| | WITHIN TWO WEEKS OF ENROLLMENT | WEEK -8 | WEEK 0 | WEEK 1 | WEEK 2 | WEEK 3 | WEEK 4 | WEEK 5 | WEEK 6 | WEEK 7 | WEEK 8 | WEEK 13 | WEEK 26 | WEEK 39 | WEEK 52 |
|---|---|---|---|---|---|---|---|---|---|---|---|---|---|---|---|
| ELIGIBILITY/CONSENT | X | | | | | | | | | | | | | | |
| MEDICATION REVIEW | X | | X | | | | | | | | | X | X | X | X |
| REVIEW OF PATIENT DIARY/AES | | | X | X | X | X | X | $X^4$ | $X^4$ | $X^4$ | $X^4$ | X | X | X | X |
| PREGNANCY TEST | X | | | | | | | | | | | | | | |
| MMSE | X | | | | | | | | | | | | | | |
| FAT BIOPSY | | $X^2$ | | | | | | | | | | | | | |
| MSC TREATMENT | | | X | | | | | | | | | | | | |
| BLOOD[1] | X | | X | X | | X | $X^4$ | $X^4$ | | $X^4$ | | | | | X |
| CSF | | | X | X | | | X | $X^4$ | | | $X^4$ | | | | |
| MRI BRAIN & SPINALCORD | | | | | | $X^3$ | | | | $X^4$ | | | | | X |
| UMSARS I | X | | | | | | | | | | | | | | |
| UMSARS I-IV | | | X | | | | | | | | | X | X | X | X |
| COMPASS | | | X | | | | | | | | | | X | | X |
| ARS | | | X | | | | | | | | | | X | | X |
| TST | | | X | | | | | | | | | | | | X |
| STUDY PHYSICIAN AND COORDINATOR VISIT | | | X | | | X | | $X^4$ | $X^4$ | $X^4$ | $X^4$ | | X | | X |
| GME AND NEURO EXAM | | | X | | | X | | $X^4$ | | $X^4$ | | | X | | X |
| TELEPHONE VISIT | | | | | | | | | | | | X | | X | |

[1] BLOOD DRAW INCLUDES SEDIMENTATION RATE, CRP, CBC (WITH DIFFERENTIAL), SODIUM, AST, INR, AND CREATININE (MAY BE OMITTED ON SCREENING DAY IF OBTAINED WITHIN 2 MONTHS OF STUDY ENROLLMENT)
[2] A SECOND BIOPSY WILL BE DONE WITHIN FOUR WEEKS OF THE INITIAL BIOPSY IF THE SECOND BIOPSY SAMPLE DOES NOT GROW CELLS
[3] GROUP 1 ONLY
[4] GROUP 2 AND 3 ONLY

FIG. 2

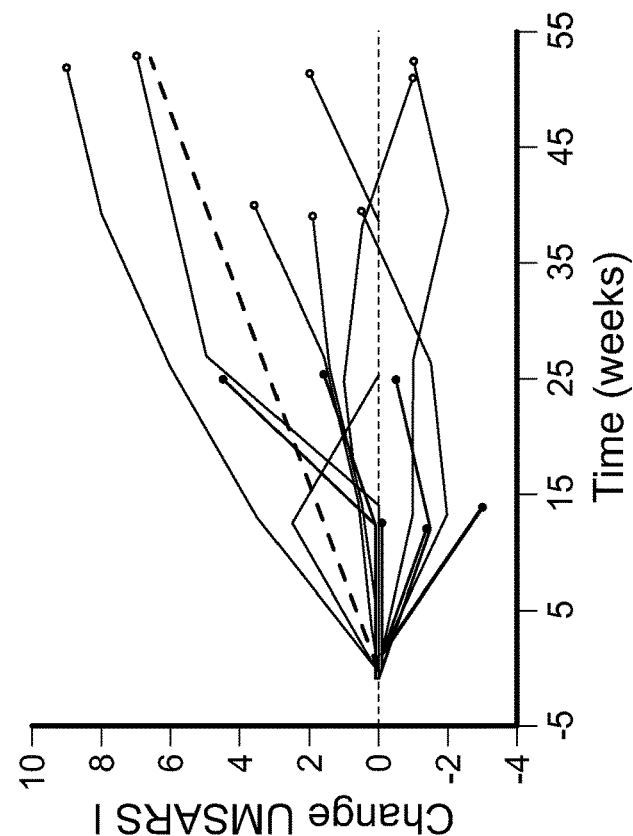
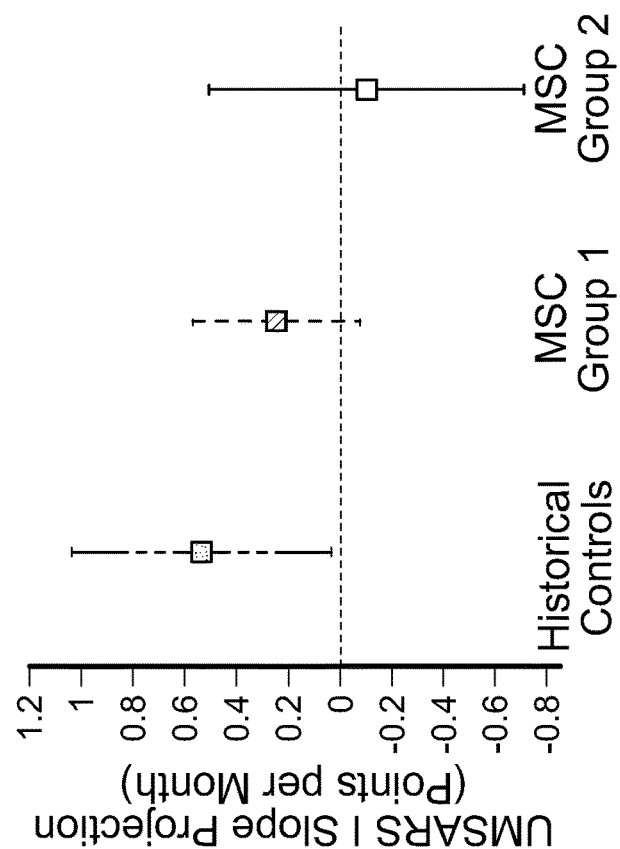
FIG. 3

TABLE 1: GENES ENRICHED IN AMSCS VS BMSCS

| CHR | GENEID | AMSC 1 | AMSC 2 | AMSC 3 | AMSC 4 | AMSC 5 | AMSC 6 | AMSC 7 | AVG AMSC | BMSC 1 | BMSC 2 | BMSC 3 | BMSC 4 | BMSC 5 | BMSC 6 | BMSC 7 | BMSC 8 | AVG BMSC | AMSC VS BMSC FOLD CHANGE |
|---|---|---|---|---|---|---|---|---|---|---|---|---|---|---|---|---|---|---|---|
| CHRX | MIR450A2 | 1.192618 | 1.907064 | 1.723135 | 0.457157 | 0.870257 | 1.552846 | 0.26112 | 1.137742 | 0 | 0 | 0 | 0 | 0 | 0 | 0 | 0 | 0 | #DIV/0! |
| CHR2 | PAX3 | 0.634871 | 0.595235 | 0.592238 | 0.105285 | 0.246133 | 0.207046 | 1.43695 | 0.545394 | 0 | 0 | 0 | 0 | 0 | 0 | 0 | 0 | 0 | #DIV/0! |
| CHR11 | MMP27 | 0.054309 | 0.057895 | 0.07473 | 0.194299 | 0.334647 | 0.125711 | 2.15618 | 0.428253 | 0 | 0 | 0 | 0 | 0 | 0 | 0 | 0 | 0 | #DIV/0! |
| CHR18 | LOC729950 | 0.141305 | 0.051354 | 0.031818 | 0.305296 | 0.099986 | 0.100356 | 1.215034 | 0.277878 | 0 | 0 | 0 | 0 | 0 | 0 | 0 | 0 | 0 | #DIV/0! |
| CHR4 | HPGD | 0.137898 | 0.01575 | 0.024397 | 0.022654 | 0.047916 | 0.0171 | 0.146648 | 0.059909 | 0 | 0 | 0 | 0 | 0 | 0 | 0 | 0 | 0 | #DIV/0! |
| CHRX | MIR503 | 58.79101 | 82.59467 | 56.51327 | 23.50172 | 72.72574 | 159.2943 | 26.84752 | 68.60974 | 0 | 0.432524 | 0.430557 | 0.539681 | 0 | 0 | 0.322128 | 0.723507 | 0.30605 | 224.1785 |
| CHR4 | ADH1B | 21.68901 | 29.41124 | 18.05372 | 0.963063 | 0.118976 | 0.829883 | 14.10748 | 12.16762 | 0.14708 | 0.171752 | 0 | 0.142869 | 0.01088 | 0 | 0.025583 | 0.047883 | 0.068256 | 178.265 |
| CHRX | ITM2A | 0.065028 | 0.467927 | 0.577152 | 3.315259 | 0.537782 | 0.564466 | 3.061109 | 1.226961 | 0.021509 | 0.016744 | 0 | 0.020893 | 0 | 0 | 0 | 0 | 0.007393 | 165.9573 |
| CHR21 | PCBP3 | 7.420133 | 11.8772 | 6.967785 | 10.14755 | 8.428844 | 9.902091 | 32.66294 | 12.48679 | 0.039665 | 0 | 0.046108 | 0.192646 | 0.322759 | 0.147782 | 0.022998 | 0 | 0.096495 | 129.4038 |
| CHR1 | FMO1 | 0.574992 | 1.480083 | 1.424174 | 7.504597 | 3.970601 | 3.092057 | 8.916883 | 3.851912 | 0 | 0 | 0.028758 | 0.05407 | 0.205682 | 0.032244 | 0 | 0 | 0.036089 | 106.7346 |
| CHR7 | ZNF467 | 1.452178 | 1.328418 | 2.138661 | 2.59771 | 2.494814 | 2.985678 | 1.40929 | 2.05825 | 0 | 0 | 0 | 0 | 0.115236 | 0.032244 | 0.020071 | 0.01127 | 0.022353 | 92.08056 |
| CHRX | MGC16121 | 56.48244 | 89.68175 | 62.44875 | 36.64234 | 82.8922 | 150.7077 | 21.3281 | 71.45475 | 0.552057 | 0.273491 | 0.972314 | 1.169995 | 0.891003 | 0.514206 | 1.454903 | 1.764584 | 0.949069 | 75.2893 |
| CHR7 | SEMA3D | 0.485966 | 1.298955 | 1.286274 | 7.454914 | 3.504392 | 2.66748 | 0.454811 | 2.450399 | 0.012607 | 0.009814 | 0.146546 | 0.055106 | 0.037303 | 0.005871 | 0.025583 | 0 | 0.033863 | 72.36238 |
| CHR12 | SLC6A15 | 1.171172 | 1.030632 | 0.919851 | 2.716938 | 1.971888 | 2.033229 | 4.239325 | 2.011862 | 0.11571 | 0.007833 | 0.031189 | 0.048868 | 0.037215 | 0.009372 | 0.003655 | 0.003276 | 0.031683 | 63.50005 |
| CHR8 | NEFL | 0.864216 | 1.129462 | 1.317255 | 3.223542 | 3.630115 | 2.048533 | 1.433684 | 1.949544 | 0.021988 | 0 | 0.00652 | 0.16019 | 0.056929 | 0 | 0 | 0 | 0.030953 | 62.9832 |
| CHR17 | CCL11 | 1.093919 | 3.556417 | 2.421703 | 0.123556 | 0.972179 | 4.112943 | 0.084687 | 1.766772 | 0.042645 | 0 | 0.033048 | 0.041424 | 0.094639 | 0.039721 | 0 | 0 | 0.031435 | 56.20438 |
| CHR14 | NOVA1 | 1.61897 | 1.072196 | 1.577594 | 2.663463 | 2.088942 | 2.23162 | 4.284043 | 2.219547 | 0.064351 | 0.007157 | 0.099738 | 0.098227 | 0.095205 | 0 | 0 | 0 | 0.045585 | 48.69074 |
| CHRX | XPNPEP2 | 9.92059 | 4.749064 | 10.07396 | 6.18595 | 0.922565 | 2.143141 | 6.870748 | 5.839003 | 0 | 0.009214 | 0 | 0.965694 | 0.043775 | 0 | 0.013724 | 0.015412 | 0.130977 | 44.57262 |
| CHR8 | FER1L6 | 1.0446 | 0.193339 | 0.122044 | 1.201255 | 0.345169 | 0.205301 | 5.33373 | 1.206448 | 0.039114 | 0.076126 | 0.010104 | 0.018997 | 0.024112 | 0.24288 | 0.011339 | 0.050936 | 0.031877 | 37.8468 |
| CHR8 | SCARA5 | 0.186751 | 0.022971 | 0.079294 | 0.401981 | 0.600997 | 0.130931 | 30.33292 | 4.679406 | 0.351611 | 0.081378 | 0 | 0 | 0.014059 | 0.008851 | 0.038568 | 0.532129 | 0.128325 | 36.46536 |
| CHR13 | SGCG | 2.035737 | 0.777806 | 2.364941 | 5.648856 | 0.122695 | 0.312758 | 0.283997 | 1.649541 | 0.023835 | 0.092777 | 0.018471 | 0.069457 | 0.035263 | 0.022201 | 0.110555 | 0 | 0.04657 | 35.42073 |
| CHR18 | EPB41L3 | 23.04896 | 25.89721 | 25.81214 | 33.3562 | 35.70287 | 30.54931 | 42.20437 | 30.93872 | 0.008872 | 0.006907 | 0.171894 | 6.222475 | 0.190335 | 0.256188 | 0.036009 | 0.144425 | 0.879638 | 35.1721 |
| CHR16 | FOXF1 | 1.477971 | 1.563167 | 0.345895 | 1.026016 | 0.384969 | 0.585903 | 3.220681 | 1.229229 | 0.008872 | 0 | 0.171894 | 0.269209 | 0.01139 | 0 | 0.008927 | 0 | 0.036191 | 33.96537 |
| CHR17 | AOC3 | 4.785286 | 3.168869 | 11.46106 | 1.147151 | 0.208006 | 0.93235 | 0.142724 | 3.120878 | 0.107805 | 0.076296 | 0.01519 | 0.447432 | 0.050748 | 0.009129 | 0.011365 | 0.019144 | 0.092139 | 33.87156 |

FIG. 4

| | | | | | | | | | | | | |
|---|---|---|---|---|---|---|---|---|---|---|---|---|
| CHR16 | VAT1L | 2.050504 | 5.133527 | 2.085122 | 5.759982 | 4.690979 | 1.381315 | 6.864274 | 3.9951 | 0.010474 | 0 | 0.056821 | 0.254364 | 0.534638 | 0.156101 | 0 | 0.00682 | 0.127402 | 31.35816 |
| CHR2 | HOXD1 | 0.996364 | 2.667476 | 2.61742 | 1.828627 | 4.112609 | 2.529107 | 0.542071 | 2.184811 | 0 | 0 | 0.061913 | 0.446227 | 0.044325 | 0.018604 | 0 | 0 | 0.071384 | 30.60662 |
| CHR20 | ADAM33 | 55.64872 | 59.70075 | 21.62225 | 55.9072 | 45.52014 | 45.52014 | 93.41394 | 54.2994 | 0.650163 | 0.05236 | 2.145689 | 6.686664 | 2.296946 | 0.27747 | 1.364855 | 1.153211 | 1.827545 | 29.71166 |
| CHR15 | CILP | 0.188847 | 0.022942 | 0.639096 | 4.936843 | 0.525894 | 0.525894 | 0.987673 | 1.211273 | 0.176575 | 0.020619 | 0.006842 | 0.04288 | 0.019593 | 0 | 0.020475 | 0.04024 | 0.040903 | 29.61323 |
| CHR1 | AIM2 | 0.642921 | 0.385525 | 0.447869 | 0.954977 | 5.356032 | 2.61598 | 5.401871 | 2.257882 | 0.079745 | 0 | 0.061798 | 0.103281 | 0.196633 | 0.198072 | 0 | 0 | 0.079941 | 28.2443 |
| CHR9 | ASPN | 47.35741 | 44.10652 | 35.11028 | 95.05384 | 51.7879 | 45.94758 | 14.30779 | 47.66733 | 0.25006 | 1.715529 | 0.38757 | 7.21107 | 3.375858 | 0.189244 | 0.471195 | 0.315459 | 1.739498 | 27.40292 |
| CHR17 | ASPA | 3.759801 | 2.121818 | 3.817753 | 0.369918 | 0.352093 | 0.541 | 2.28898 | 1.890023 | 0.186196 | 0.020707 | 0 | 0.077513 | 0.05903 | 0 | 0.123377 | 0.085596 | 0.069178 | 27.36472 |
| CHR13 | TEX29 | 1.135426 | 1.781989 | 0.798551 | 0.677031 | 1.350188 | 1.241108 | 5.598054 | 1.797478 | 0.111275 | 0.043313 | 0 | 0.246942 | 0.051823 | 0 | 0.072453 | 0.063726 | 27.34814 |
| CHR15 | PCSK6 | 1.73766 | 1.656675 | 2.501722 | 1.318656 | 2.098364 | 0.997943 | 0.636116 | 1.563905 | 0.023582 | 0.032127 | 0.059394 | 0.292062 | 0.004361 | 0.005491 | 0.051273 | 0.007677 | 0.0594495 | 26.28591 |
| CHRX | CLIC2 | 1.476342 | 1.508753 | 1.347201 | 3.208267 | 0.831594 | 0.896095 | 7.825815 | 2.44201 | 0.073431 | 0.457322 | 0.045524 | 0.085593 | 0.032592 | 0.005491 | 0.068119 | 0.009562 | 0.096518 | 25.30108 |
| CHR17 | HOXB8 | 1.253847 | 1.098419 | 1.228785 | 2.984183 | 1.798118 | 2.782572 | 4.483296 | 2.233531 | 0.086554 | 0.117918 | 0 | 0 | 0.144061 | 0.342633 | 0.012546 | 0.028178 | 0.091485 | 24.41385 |
| CHR2O | CPXM1 | 15.57857 | 13.98514 | 17.34417 | 34.63915 | 14.5889 | 12.42277 | 87.18135 | 27.96286 | 0.147926 | 0.025591 | 0.343907 | 0.542829 | 8.316403 | 0.321496 | 0.038118 | 0.010702 | 1.218372 | 22.95101 |
| CHR4 | NBLA00301 | 2.84142 | 0.466807 | 3.310012 | 2.417082 | 1.590549 | 1.790705 | 2.999809 | 2.202341 | 0 | 0 | 0.119724 | 0.650294 | 0 | 0 | 0 | 0 | 0.096252 | 22.88091 |
| CHR2 | DIRC1 | 0.738209 | 1.737868 | 1.168169 | 0.770312 | 0.45887 | 0.961184 | 2.729725 | 1.223477 | 0.18991 | 0.063361 | 0.021024 | 0 | 0.080276 | 0.02527 | 0.01573 | 0.035329 | 0.053863 | 22.71478 |
| CHR11 | MMP3 | 0.326208 | 0.417301 | 0.915701 | 1.875643 | 18.43981 | 60.63357 | 10.98474 | 13.37114 | 1.596858 | 0.823167 | 1.772633 | 0.104807 | 0.223482 | 0.381895 | 0.050045 | 0.042152 | 0.624381 | 21.41502 |
| CHR1 | DPT | 5.797447 | 21.05165 | 26.96671 | 153.9068 | 72.8572 | 78.16649 | 54.32439 | 59.0101 | 0.502218 | 0.390973 | 2.352865 | 9.202372 | 8.342071 | 0.955832 | 0.463245 | 0.074319 | 2.785612 | 21.18389 |
| CHR2 | HOXD-AS1 | 2.632849 | 6.239933 | 5.220836 | 5.502702 | 7.135882 | 4.713631 | 2.202876 | 4.806959 | 0.134773 | 0.153344 | 0.305294 | 0.76534 | 0.14571 | 0.077251 | 0.114205 | 0.128254 | 0.228021 | 21.08118 |
| CHR11 | H19 | 664.0395 | 345.9652 | 1494.048 | 1247.713 | 389.8603 | 222.745 | 556.848 | 703.0056 | 0.23928 | 0.266111 | 1.920531 | 244.8127 | 29.05393 | 1.050691 | 5.628582 | 0.94592 | 35.48971 | 19.80872 |
| CHR9 | OGN | 4.782914 | 6.210239 | 3.892684 | 27.99284 | 11.00945 | 13.10493 | 29.38129 | 13.76776 | 0.28928 | 0.060077 | 0.039869 | 2.611127 | 2.169261 | 0.107819 | 0.134229 | 0.334979 | 0.71754 | 19.18746 |
| CHR1 | TNFRSF9 | 0.179102 | 0.795538 | 0.172515 | 0.789517 | 3.005895 | 4.750348 | 0.501064 | 1.456283 | 0.09215 | 0.071738 | 0.071412 | 0.127874 | 0.068167 | 0.018393 | 0.095407 | 0.077143 | 0.077786 | 18.72173 |
| CHR11 | PDGFD | 30.5472 | 31.0083 | 46.4829 | 59.07661 | 30.08378 | 38.20216 | 58.40372 | 41.97209 | 7.488303 | 0.39919 | 0.934006 | 1.228305 | 4.026642 | 0.202437 | 1.32312 | 2.708032 | 2.288846 | 18.33767 |
| CHR12 | INHBE | 20.93321 | 23.05575 | 15.7071 | 3.779938 | 7.868146 | 17.5335 | 0.24644 | 12.73201 | 0.226614 | 0.10081 | 0.689916 | 0.110062 | 0.981859 | 0.015077 | 1.510973 | 2.24489 | 0.735025 | 17.32187 |
| CHR20 | FAM65C | 3.168892 | 2.745219 | 4.519584 | 2.402716 | 0.989314 | 0.949143 | 14.07765 | 4.121789 | 0.331719 | 0.164987 | 0.149956 | 0.223764 | 0.749787 | 0.060079 | 0.144246 | 0.089995 | 0.239317 | 17.22315 |
| CHR11 | ADAMTS15 | 2.526643 | 0.982763 | 3.066184 | 5.456726 | 2.289613 | 1.700762 | 55.33383 | 10.19379 | 0.507334 | 0.568087 | 0.156187 | 1.552676 | 0.66319 | 0.368977 | 0.165207 | 0.782843 | 0.595563 | 17.11623 |
| CHR7 | WNT2 | 26.65538 | 15.96329 | 36.75489 | 10.17827 | 24.78607 | 17.07275 | 37.62245 | 24.14759 | 0 | 0.496673 | 0.010519 | 5.564322 | 3.695242 | 1.264362 | 0.243979 | 0.574498 | 1.4812 | 16.30272 |
| CHR1 | S100A4 | 205.642 | 211.3747 | 252.0979 | 292.0454 | 407.3545 | 327.8689 | 1583.525 | 468.5583 | 26.57774 | 6.316073 | 9.810442 | 94.97811 | 13.65889 | 63.1265 | 9.286303 | 8.607039 | 29.04514 | 16.13207 |
| CHR12 | TBX5 | 1.3431 | 0.268462 | 1.216383 | 1.959544 | 1.306753 | 1.48111 | 2.79564 | 1.481713 | 0.061781 | 0.12024 | 0.071816 | 0.688912 | 0.006707 | 0.016889 | 0.01577 | 0.017709 | 0.092998 | 15.93269 |
| CHR11 | TNNT3 | 3.198681 | 5.413553 | 11.08404 | 22.08816 | 6.065224 | 4.357372 | 8.342745 | 8.649967 | 0.133537 | 0 | 0 | 3.840737 | 0.182806 | 0 | 0.14328 | 0.040226 | 0.557611 | 15.51256 |
| CHR11 | LOC650368 | 2.866481 | 0.209816 | 1.663302 | 3.807061 | 3.928041 | 2.137147 | 4.596556 | 2.747001 | 0.133537 | 0 | 0.0269062 | 0.155656 | 0.612452 | 0.124382 | 0.108394 | 0.01739 | 0.177609 | 15.46656 |

FIG. 4 (Cont.)

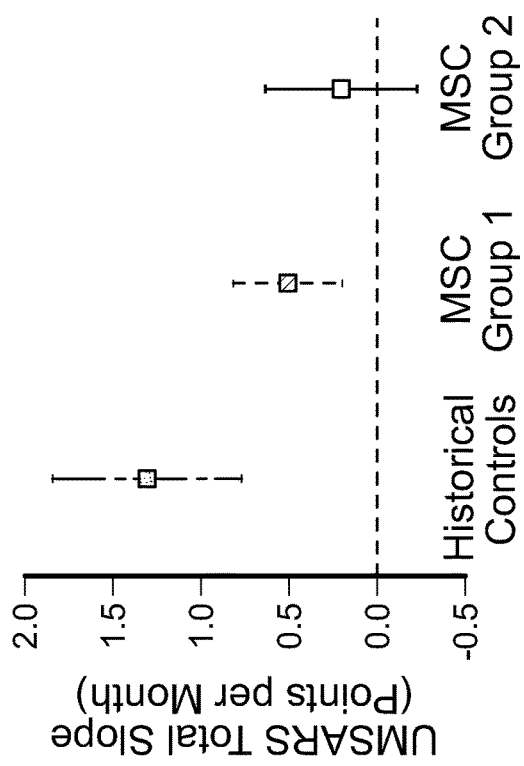
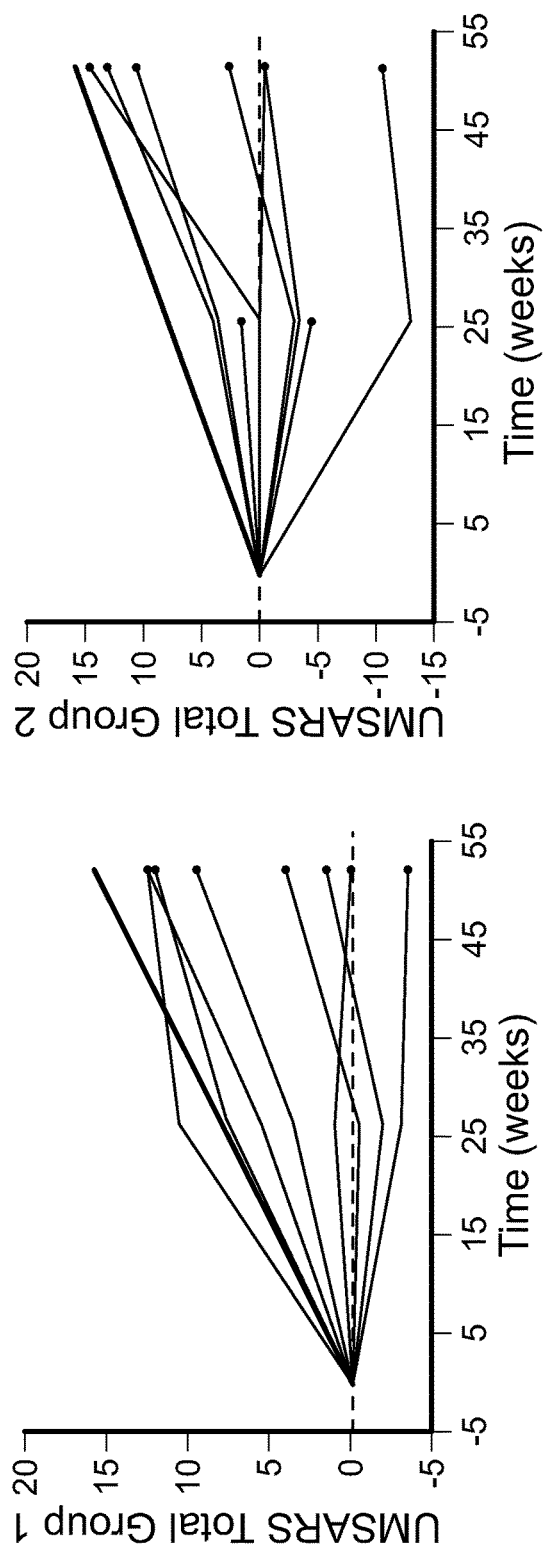
FIG. 5

USING AUTOLOGOUS MESENCHYMAL STEM CELLS TO TREAT MULTIPLE SYSTEM ATROPHY

CROSS-REFERENCE TO RELATED APPLICATIONS

This application is a National Stage application under 35 U.S.C. § 371 of International Application No. PCT/US2016/037632, having an International Filing Date of Jun. 15, 2016, which claims priority to U.S. Application Ser. No. 62/175,628, filed on Jun. 15, 2015. The disclosure of the prior application are considered part of the disclosure of this application, and are incorporated in its entirety into this application.

BACKGROUND

1. Technical Field

This document relates to methods and materials for treating multiple system atrophy. For example, this document provides methods and materials for intrathecally administering autologous mesenchymal stem cells (e.g., adipose derived mesenchymal stem cells) to mammals (e.g., humans) to treat multiple system atrophy.

2. Background Information

Multiple system atrophy is a sporadic and fatal multisystem progressive disorder characterized by progressive autonomic failure, orthostatic hypotension, neurogenic bladder/erectile dysfunction, cerebellar ataxia, corticospinal dysfunction, and Parkinsonism. Multiple system atrophy progresses relentlessly and survival from diagnosis to death is 2-4 years. Multiple system atrophy is a rare disease with a prevalence of 3-5 per 100,000. The prevalence is 28/100,000 in persons over the age of 65.

SUMMARY

This document provides methods and materials for treating multiple system atrophy. For example, this document provides methods and materials for using autologous mesenchymal stem cells (e.g., adipose derived mesenchymal stem cells) to treat multiple system atrophy.

As described herein, autologous adipose derived mesenchymal stem cells can be safely administered intrathecally to humans suffering from multiple system atrophy to improve one or more symptoms of multiple system atrophy and/or to slow the progression of multiple system atrophy.

In general, one aspect of this document features a method of treating a mammal having multiple system atrophy. The method comprises, or consist essentially of, intrathecally administering, to the mammal, a composition comprising autologous mesenchymal stem cells. The mammal can be a human. The composition can comprise from about $5 \times 10^6$ to about $5 \times 10^8$ autologous mesenchymal stem cells. The rate of progression of the multiple system atrophy can be reduced following the administering step. The autologous mesenchymal stem cells can be adipose derived mesenchymal stem cells or bone marrow derived mesenchymal stem cells. The method can comprise intrathecally administering the composition comprising autologous mesenchymal stem cells more than one time to the mammal. The method can comprise intrathecally administering the composition comprising autologous mesenchymal stem cells to the mammal two to ten times.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF THE DRAWINGS

FIG. 2 is a test schedule table.

FIG. 3 is contains graphs plotting UMSARS I progression in historical controls versus patients who received an intrathecal administration of autologous mesenchymal stem cells. The left panel shows the projected UMSARS I change per month by group, while the right panel shows the change of UMSARS I over time in individual patients following injection of autologous mesenchymal stem cells (thin solid lines—low dose group grey, middle dose group black) versus the expected change (thick dashed line).

FIG. 4 is a graph plotting the results of an RNA-seq analysis, which was performed for seven different adipose derived mesenchymal stem cell lines and eight different bone marrow derived mesenchymal stem cells. All cell lines were evaluated at confluence. A fold change comparison for all genes expressed at greater than 1 reads per kilobase per million (RPKM) was made. Top 50 genes enriched in adipose derived mesenchymal stem cells are listed.

FIG. 5 contains graphs of UMSARS total progression in historical controls and patients who received intrathecal administration of autologous mesenchymal stem cells (group 1=10 million cells; group 2=50 million cells given twice). The top panel shows the change in UMSARS total as mean and standard deviation for each group. The bottom panels show the individual change of UMSARS total over time for patients in group 1 (bottom; left) and group 2 (bottom; right) compared to the average change seen in historical controls (thick line). Note than all patients treated with autologous mesenchymal stem cells exhibited slower disease progression than the average of the control group. Some patients experienced no progression or even improvement at the 6 and 12 month follow-up evaluations.

DETAILED DESCRIPTION

Figure 1:
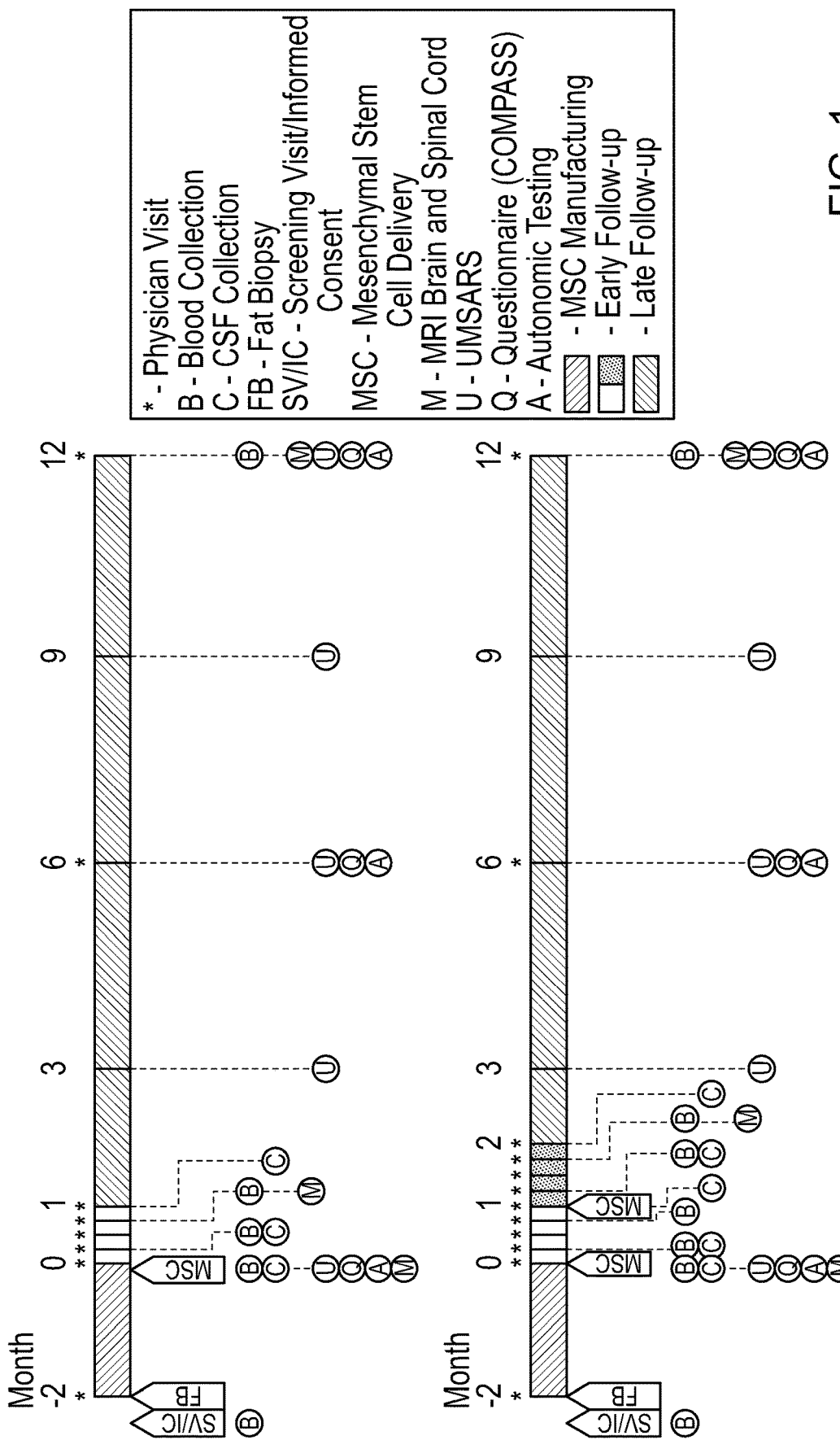
FIG. 1 is a schematic of a patient treatment protocol.

This document provides methods and materials for treating multiple system atrophy. For example, this document provides methods and materials for using autologous mesenchymal stem cells to treat multiple system atrophy. As described herein, mesenchymal stem cells can be administered intrathecally to a mammal suffering from multiple system atrophy to improve one or more symptoms of multiple system atrophy and/or to slow the progression of multiple system atrophy. Examples of mesenchymal stem cells that can be administered intrathecally to treat multiple system atrophy include, without limitation, autologous adipose derived mesenchymal stem cells and autologous bone marrow derived mesenchymal stem cells.

In some cases, adipose derived mesenchymal stem cells expressing the genes listed in FIG. 4 or having expression levels within the range shown for AMSC1-7 in FIG. 4 can be administered intrathecally to a mammal suffering from multiple system atrophy to improve one or more symptoms of multiple system atrophy and/or to slow the progression of multiple system atrophy.

In some cases, multiple system atrophy can be treated by administering (e.g., via intrathecal administration) an effective amount of a composition that includes autologous mesenchymal stem cells (e.g., adipose derived mesenchymal stem cells). Effective amounts of a composition containing autologous mesenchymal stem cells (e.g., adipose derived mesenchymal stem cells) can be determined by a physician, taking into account various factors such as overall health status, body weight, sex, diet, time and route of administration, other medications, and any other relevant clinical factors. As used herein, an "effective amount" or "therapeutically effective amount" of a composition is the amount that is sufficient to provide a beneficial effect to the subject to which the composition or preparations are delivered. The effective amount can be the amount effective to achieve an improved survival rate, a more rapid recovery, an improvement in the quality of life, or an improvement or elimination of one or more symptoms associated with a subject's multiple system atrophy.

In some cases, a composition containing from about $5 \times 10^6$ to about $5 \times 10^8$ autologous mesenchymal stem cells (e.g., adipose derived mesenchymal stem cells) can be administered intrathecally to a mammal to treat multiple system atrophy. For example, about $5 \times 10^7$ (±about 20%) autologous mesenchymal stem cells (e.g., adipose derived mesenchymal stem cells) can be administered intrathecally to a mammal to treat multiple system atrophy. In some cases, multiple (e.g., two, three, four, five, or more) treatments of cells can be performed to obtain or maintain an effect.

Any appropriate method can be used to obtain autologous mesenchymal stem cells (e.g., adipose derived mesenchymal stem cells). For example, the techniques described elsewhere can be used to obtain autologous mesenchymal stem cells (e.g., adipose derived mesenchymal stem cells). See, e.g., Zuk et al., *Tissue Engineering*, 7(2):211-228 (2001) and Sotiropoulou et al., *Stem Cells*, 24:462-471 (2006).

In some cases, autologous mesenchymal stem cells can be obtained as follows. After harvesting adipose tissue, the tissue can be fragmented, cut into small pieces, and washed in PBS. Discolored tissue and excess vasculature can be removed, and the tissue can be diced. The tissue can be re-suspended in about 0.075% Collagenase (Worthington Biochemical Corporation) in Hank's buffer and incubated at about 37° C. The tube can be inverted until the visible evidence of tissue is lost. The tissue digest can be washed by centrifugation in full media (Advanced MEM low glucose, 5% human platelet lysate, 2 Units per mL Heparin). In some cases, the cells can be passed through filters (e.g., 70 μm and/or 40 μm filters) to remove large tissue pieces. The cells can be plated and maintained at less than 90% confluency and passaged when needed using 0.25% Trypsin EDTA. The cells can be expanded to obtain an appropriate number, and cryopreserved to complete release testing. In some cases, the cells can be thawed and returned to culture conditions for 3-5 days prior to collection, washing, and preparation for infusion.

A composition containing autologous mesenchymal stem cells (e.g., adipose derived mesenchymal stem cells) can be administered one or more than one time to the same mammal (e.g., human). For example, a composition containing autologous mesenchymal stem cells (e.g., adipose derived mesenchymal stem cells) can be administered intrathecally to a human at least monthly (e.g., about monthly ±4 days) for two to 36 months.

Any appropriate mammal can be treated as described herein. For example, humans, non-human primates (e.g., chimpanzees, baboons, or monkeys), horses, dogs, cats, rabbits, mice, or rats can be treated as described herein.

In some cases, the methods described herein can include monitoring multiple system atrophy in the mammal to, for example, determine if the multiple system atrophy is improving with treatment. Any appropriate method can be used to monitor multiple system atrophy. For example, neurologic examination, MSA rating score (UMSARS), autonomic function testing, MRI measurements of the brain, and/or PET/SPECT imaging can be used to monitor the progression of multiple system atrophy.

In some cases, the methods and materials provided herein can be used to treat conditions other than multiple system atrophy. For example, the methods and materials provided herein can be used to treat Parkinson's disease, diffuse Lewy-body disease, Lewy-body dementia, pure autonomic failure, and/or tauopathies such as Alzheimer's disease, frontotemporal dementia, corticobasal degeneration, and progressive supranuclear palsy. In some cases, mesenchymal stem cells can be administered intrathecally to a mammal suffering from one or more of these other conditions to improve one or more symptoms of those conditions and/or to slow the progression of those conditions.

The invention will be further described in the following examples, which do not limit the scope of the invention described in the claims.

EXAMPLES

Example 1

Intrathecal Administration of Autologous Mesenchymal Stem Cells

Rabbits were injected with $1 \times 10^7$ autologous mesenchymal stem cells via single injections per rabbit or three injections per rabbit over a course of 12 weeks. Animals were monitored for acute and chronic adverse events including: subarachnoid irritation, aseptic meningitis with pain or seizures, and unregulated growth of cells to form intrathecal tumors. Ratios of the organ to the body weight were measured and calculated for each rabbit. Macroscopic examination was conducted for each organ.

There were no significant or abnormal findings except in one rabbit that exhibited a small accumulation of mesenchymal cells in the subarachnoid space in the region of the injection, and one that exhibited a small inflammatory cell collection in the extradural space in the region of the injection.

Blood test results did not reveal any significant difference between control and experimental groups after both 4 and 12 weeks. There were no significant differences for the organ to body weight ratios between control and experimental groups. Macroscopic and microscopic examinations also did not reveal any meaningful difference between the control and experimental groups. Functional assessments did not reveal a difference directly related to the injection of mesenchymal stem cells.

These results demonstrate that mesenchymal stem cells can be safely injected into that CSF via, for example, intrathecal administration.

Example 2

Intrathecal Administration of Autologous Mesenchymal Stem Dells Into a Human

A human patient with amyotrophic lateral sclerosis (ALS) was administered $1 \times 10^6$ autologous mesenchymal stem cells. The patient tolerated the procedure well, with stable vital signs and no fevers. Spinal fluid analyses at one and three weeks after mesenchymal stem cell administration were stable when compared to baseline studies. No adverse events associated with the administered mesenchymal stem cells were noted.

The patient's ALS progressed at an expected rate, and the patient passed away from the disease.

Example 3

Intrathecal Administration of Autologous Mesenchymal Stem Cells to Treat Multiple System Atrophy Mesenchymal stem cells are isolated from a fat biopsy obtained from a human with multiple system atrophy. The mesenchymal stem cells are expanded and released for human use after meeting release criteria. Briefly, after harvesting, the adipose tissue is fragmented, cut into small pieces, and washed in PBS. Discolored tissue and excess vasculature is removed, and the tissue is diced. The tissue is re-suspended in 0.075% Collagenase (Worthington Biochemical Corporation) in Hank's buffer and incubated at 37° C. The tube is inverted until the visible evidence of tissue is lost. The tissue digest is washed by centrifugation in full media (Advanced MEM low glucose, 5% human platelet lysate, 2 units per mL Heparin). In some cases, the cells are passed through filters (e.g., 70 μm and 40 μm filters) to remove large tissue pieces. Cells are plated and maintained at less than 90% confluency and are passaged when needed using 0.25% Trypsin EDTA. Cells are expanded and cryopreserved to complete release testing. In some cases, cells are thawed and returned to culture conditions for 3-5 days prior to collection, washing, and preparation for infusion.

Once released, the mesenchymal stem cells (e.g., from about $1 \times 10^7$ to about $1 \times 10^8$ cells) are injected intrathecally into that same human with multiple system atrophy. In some cases, subsequent intrathecal injections of from about $1 \times 10^7$ to about $1 \times 10^8$ mesenchymal stem cells are administered to the human monthly, every other month, every 6 months, or every year for up to about 3 years.

Example 4

Clinical Study to Evaluate Treating Multiple System Atrophy

Twenty-four adult humans with multiple system atrophy (probable, based on Gilman criteria) and UMSARS I score ≤17 are selected in order to exclude cases that are very advanced. Briefly, the inclusion criteria are: (1) participants aged 30-80 years with a diagnosis of multiple system atrophy based on clinical criteria and standardized autonomic testing. This approach allows for identification of patients with multiple system atrophy with very high specificity and is yet sensitive enough to allow for enrollment of patients at a disease stage at which an intervention on the natural disease course has a meaningful impact on patient outcome. Patients therefore are selected to fulfill Gilman Criteria for probable multiple system atrophy of the parkinsonian subtype (MSA-P) or cerebellar subtype (MSA-C), have an UMSARS I score ≤17, and have findings on autonomic function testing suggestive of multiple system atrophy (CASS≥5 and/or TST % anhidrosis≥25%); (2) participants who are less than 4 years from the time of documented MSA diagnosis; (3) participants with an anticipated survival of at least 3 years; (4) participants who are willing and able to give informed consent; and (5) "Normal" cognition as assessed by MMSE. A value >24 is required. Any of the following conditions exclude a participant: (1) Pregnant or breastfeeding women, and women of childbearing potential who do not practice an acceptable method of birth control. Acceptable methods of birth control in this study are: surgical sterilization, intrauterine devices, partner's vasectomy, a double-protection method (condom or diaphragm with spermicide), hormonal contraceptive drug (i.e., oral contraceptive, contraceptive patch, long-acting injectable contraceptive) with a required second mode of contraception; (2) participants with a clinically significant or unstable medical or surgical condition that might preclude safe completion or might affect the results. These include conditions causing significant CNS or autonomic dysfunction, including congestive heart failure, recent (<6 months) myocardial infarct, cardiopulmonary disease, severe, uncontrolled hypertension, thrombocytopenia (<50×10$^9$/L), severe anemia (<8 g/dL), immunocompromised state, liver or kidney disease (creatinine >2.3 mg/dL), uncontrolled diabetes mellitus (HbA1c>10 g %), alcoholism, malignant neoplasms, amyloidosis, uncontrolled hypothyroidism, sympathectomy, unstable peripheral neuropathies, concurrent infections, orthopedic problems that compromise mobility and activity of daily living, cerebrovascular accidents, neurotoxin or neuroactive drug exposure, parkinsonism due to drugs (including neuroleptics, alpha-methyldopa, reserpine, metoclopramide); (3) participants who have taken any investigational products within 60 days prior to baseline; (4) Medications that could affect autonomic function. If patients are taking those medications, those are suspended prior to autonomic testing. Therapy with midodrine, anticholinergic, alpha and beta adrenergic antagonists or other medications that affect autonomic function are withdrawn 48 hours prior to autonomic evaluations. Fludrocortisone doses up to 0.2 mg per day are permitted; (5) diseases with features of Parkinson's disease; e.g., diffuse Lewy body disease, progressive supranuclear palsy, essential tremor, hereditary olivopontocerebellar atrophy, or postencephalitic parkinsonism; (6) dementia (DSM-IV criteria—*Amer. Psych. Assoc.,* 1994). The score on the Mini-Mental State Examination must be >24; (7) history of electroconvulsive therapy; (8) history of brain surgery for Parkinson's disease; (9) patients with contraindication for MRI scanning, including those with MRI-incompatible pacemakers; and (10) patients with active systemic infection or local infection, which is close to the spinal injection site.

Cells are isolated from adipose tissue. Briefly, a subcutaneous fat biopsy is taken from either the abdomen or thigh of each human. The actual site of the biopsy is determined by the general surgeon, at the time of the procedure. The subject is given a local anesthetic (usually 1% lidocaine) at the site of the biopsy. The fat biopsy is done through a small (1-2 inch) incision where approximately 15 cc of subcutaneous fat is removed from under the skin. The biopsy site is sutured with an intradermal absorbable suture that will not require suture removal. The suture is reabsorbed in 1-3 weeks.

The cells are expanded ex vivo and cryo-preserved during release criteria analysis. Cells are tested for phenotype, mycoplasma, culture sterility, and cytogenetic analysis. Cells not meeting release criteria are not administered to the patient. In the event there is no cell growth from the tissue obtained from the first biopsy, one further attempt is carried out from a second biopsy. If the second attempt fails to grow cells, no further attempts are made.

After about 8 weeks, the autologous mesenchymal stem cells are administered to each human via intrathecal injection. The autologous mesenchymal stem cells are placed in syringes at 4° C. and administered within 12 hours. A lumbar spinal needle is placed in the subarachnoid space, and a baseline CSF sample is collected. This baseline CSF sample is analyzed for total nucleated cell count (with differential), total CSF protein, glucose, IgG levels, immunoglobulin synthesis rate and index, oligoclonal bands and cytology with emphasis on MSC markers. CSF (10 mL) is also retained for measurement of cytokines. The lumbar puncture is performed into the lumbar subarachnoid space via a standard posterior, intervertebral approach between lumbar level 2 and 5. The exact level is determined individually for each patient based on anatomical considerations. Next, mesenchymal stem cells are infused into the CSF in 2-10 mL of Lactated Ringers solution over 1-2 minutes via free-hand delivery, followed by a 1 mL flush with Lactated Ringers. After cell infusion and if the patient is tolerant, they are rotated every 15 minutes in a horizontal position (with help from nursing staff if necessary) for 2 hours to maximize even distribution of cells in the CSF.

The subjects are observed for any adverse events during and immediately following the intrathecal injection. The patient's vital signs (including pain) are monitored every 15 minutes for one hour, and then hourly for four hours, and then every four hours until discharge, which is at least 48 hours after injection.

Escalating doses of mesenchymal stem cells are used across three patient groups of 8 patients each (FIG. 1). Group 1 receives a single dose of cells. Groups 2 and 3 receive two doses of cells separated by one month. The lowest dose of cells delivered is $1 \times 10^7$. Group 1 patients are administered a single intrathecal dose of $1 \times 10^7$ cells. Group 2 patients are administered one intrathecal dose of $5 \times 10^7$ cells followed one month (±4 days) later by a second intrathecal dose of $5 \times 10^7$ cells. Group 3 patients are administered one intrathecal dose of $1 \times 10^8$ cells followed one month (±4 days) later by a second intrathecal dose of $1 \times 10^8$ cells.

All patients are followed on a regular basis for a minimum of 12 months (FIG. 2). Initial clinical follow-up is performed weekly with scheduled blood, CSF, and MRI evaluations for up to 8 weeks. Thereafter, patients are subjected to clinical evaluations at six and twelve months. Phone follow-ups are performed at three and nine months. Additional evaluations take place if indicated by clinical status.

In some cases, the patients of Group 1, 2, or 3 receive a dose of $5 \times 10^7$ cells (±20%) once every 6 months (±1 month) for a total of four additional intrathecal injections. The autologous mesenchymal stem cells are administered in 5 mL of Lactated Ringers solution over 1-2 minutes.

Example 5

Clinical Study to Evaluate Treating Multiple System Atrophy

Injection of all patients in groups 1 and 2 of Example 4 were completed. Each of these patients were followed for at least 8 weeks. Five patients completed one year of follow-up. In particular, 8 patients received a single dose of $1 \times 10^7$ cells, 8 patients received two doses of $5 \times 10^7$ cells, and 1 patient received two doses of $1 \times 10^8$ cells.

The safety and tolerability experience was very positive. To this point, no serious adverse event attributable to the intrathecal injection of autologous mesenchymal stem cells was observed. One patient experienced a temporary inguinal hernia incarceration four weeks after intrathecal injection which required hospitalization for observation but resolved spontaneously. This event was categorized as a severe adverse event, but was determined to be definitely not related.

Asymptomatic imaging findings of focal nerve root thickening about the cauda equina in the area of intrathecal mesenchymal stem cell administration on scheduled MRI studies (7 weeks after first, 3 weeks after second mesenchymal stem cell injection) were observed in four patients. All patients were and still are completely asymptomatic with unchanged neurological examination, and all four patients were in dose group 2. While this imaging finding was indeterminate, it was suspected that this phenomenon is an "implantation" response of mesenchymal stem cells. There was no suggestion of neural inflammation clinically nor based on CSF studies.

One patient presented imaging evidence of a subdural hematoma in the area of repeated lumbar spinal taps. This was completely asymptomatic and was only discovered incidentally on scheduled MRI imaging. There was no compromise of nerve roots or spinal cord, and a neurologic exam remained unchanged.

Three patients noticed mild to moderate headaches following at least one of the lumbar punctures, which were as expected of positional nature. All resolved spontaneously without intervention.

One patient in group 2 experienced fever 10 hours after the first mesenchymal stem cell administration. The fever lasted approximately 30 hours with a $T_{max}$ of 38.9 degrees. There was no suggestion of infection. The fever resolved spontaneously without intervention. The etiology remained indeterminate.

Two patients experienced urinary tract infections which is a common occurrence in multiple system atrophy related to bladder dysfunction, and not related to the administration of mesenchymal stem cells. Three patients reported temporary low back or buttock discomfort. One patient had temporary cramping of calf muscles, another patient noticed occasional lower extremity muscle twitching, and another patient felt an increased level of fatigue about one month after treatment. The etiology of these events was uncertain, but unlikely to be directly related to the administration of mesenchymal stem cells.

The following table summarizes adverse events by type, severity, and attribution seen in 19 patients (Table 1).

| ADVERSE EVENT | FREQUENCY | SEVERITY | ATTRIBUTION |
|---|---|---|---|
| Asymptomatic MRI imaging findings | n = 4 | Mild-Moderate | Definitely |
| Temporary headaches | n = 3 | Mild-Moderate | Possibly/Probably |
| Low back discomfort | n = 3 | Mild-Moderate | Possibly |
| Muscle cramps/twitching | n = 2 | Mild | Possibly/Probably Not |
| Urinary tract infection | n = 2 | Mild-Moderate | Definitely Not |
| Fever | n = 1 | Moderate | Possibly |
| Fatigue | n = 1 | Mild | Possibly |
| Hernia incarceration | n = 1 | Moderate | Definitely Not |

The majority of patients who had late-follow up of 3 months or more reported a benefit from the treatment. The described benefit in these patients ranged from slowing of disease progression to notable functional improvement. In contrast, the natural history of multiple system atrophy was thoroughly studied, and the disease progresses predictably at a rate of 0.375 to 0.66 points per month on the first part of the Unified Multiple System Atrophy Rating Scale (UMSARS I, a functional score of symptoms and ability to undertake activities of daily living). The placebo group, in a recently completed rifampicin treatment trial with patients enrolled at a similar disease stage as the patients for this study and essentially identical inclusion/exclusion criteria for selection, exhibited a rate of progression of 6 points over the 48 weeks of the study (0.5 points per 4 weeks). The data from this other study was used to generate a predicted progression slope ("historical controls") and contrasted that to the progression observed in the patients who received intrathecal administrations of autologous mesenchymal stem cells (FIG. 3).

Only three patients progressed or were projected to progress at or above the rate predicted. The other 11 patients progressed or were projected to progress less than predicted. In fact, several patients completed the study or were projected to complete the study with scores indicating either (a) lack of progression or (b) an improvement.

These results demonstrate that intrathecal administrations of autologous mesenchymal stem cells can be used to treat multiple system atrophy.

The twenty four patients completed one year of follow-up after receiving intrathecal mesenchymal stem cell injections. The safety and efficacy data remain highly favorable. The treatments were generally well tolerated with few adverse events. Changes on MRI imaging of the cauda equina (as described herein) were observed, and additional patients reported temporary low back and leg pain following the treatments. No attributable serious adverse events, however, were observed. On the other hand, efficacy data continued to be positive. Patients generally progressed at rates lower than expected, and some observed no disease progression, while other observed improvement through the year following treatments. None of the patients experienced a rate of progression that was faster than the average of a historical control group (FIG. 5).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for slowing the progression of multiple system atrophy at a disease stage wherein a human has a Unified Multiple System Atrophy Rating Scale I (UMSARS I) score of 17 or less, wherein said method comprises:
    (a) determining that said human having multiple system atrophy has a UMSARS I score of 17 or less,
    (b) intrathecally administering, to said human, a composition comprising autologous mesenchymal stem cells, wherein said autologous mesenchymal stem cells are adipose derived mesenchymal stem cells or bone marrow derived mesenchymal stem cells, and
    (c) determining, at least three months following said administering step, that said human has a UMSARS I score indicating no disease progression or improvement of said multiple system atrophy compared to said UMSARS I score of 17 or less.

2. The method of claim 1, wherein said composition comprises from about $5\times10^6$ to about $5\times10^8$ autologous mesenchymal stem cells.

3. The method of claim 1, wherein said method comprises intrathecally administering said composition comprising autologous mesenchymal stem cells more than one time to said human.

4. The method of claim 1, wherein said method comprises intrathecally administering said composition comprising autologous mesenchymal stem cells to said human two to ten times.

* * * * *